United States Patent
Luo et al.

(10) Patent No.: US 9,259,396 B2
(45) Date of Patent: Feb. 16, 2016

(54) METHOD OF PREPARING SOY ISOFLAVONE NANOPARTICLES BY PRECIPITATION WITH COMPRESSED ANTISOLVENT (PCA) USING A SUPERCRITICAL FLUID

(71) Applicant: Nano and Advanced Materials Institute Limited, HK (HK)

(72) Inventors: Kathy Qian Luo, Hong Kong (HK); Jinjie Xu, Hong Kong (HK)

(73) Assignee: NANO AND ADVANCED MATERIALS INSTITUTE LIMITED, Hong Kong (HK)

( * ) Notice: Subject to any disclaimer, the term of this patent is extended or adjusted under 35 U.S.C. 154(b) by 0 days.

(21) Appl. No.: 13/733,901

(22) Filed: Jan. 4, 2013

(65) Prior Publication Data

US 2013/0190392 A1    Jul. 25, 2013

Related U.S. Application Data (60) Provisional application No. 61/632,212, filed on Jan. 20, 2012.

(51) Int. Cl.
| | |
|---|---|
| *A61K 31/352* | (2006.01) |
| *A61K 9/51* | (2006.01) |
| *C07D 311/36* | (2006.01) |
| *A61K 9/00* | (2006.01) |

(52) U.S. Cl.
CPC ............. *A61K 9/5192* (2013.01); *A61K 31/352* (2013.01); *C07D 311/36* (2013.01); *A61K 9/0053* (2013.01); *A61K 9/0075* (2013.01)

(58) Field of Classification Search
None
See application file for complete search history.

(56) References Cited

U.S. PATENT DOCUMENTS

| | | | | |
|---|---|---|---|---|
| 5,554,519 | A | * 9/1996 | Weber et al. | ........... 435/125 |
| 5,874,029 | A | 2/1999 | Subramaniam et al. | |
| 6,319,521 | B1 | 11/2001 | Randolph et al. | |
| 6,517,840 | B1 | * 2/2003 | Kozak et al. | ........... 424/757 |

(Continued)

FOREIGN PATENT DOCUMENTS

| | | |
|---|---|---|
| CN | 1397555 A | 2/2003 |
| CN | 100523158 C * | 8/2009 |

OTHER PUBLICATIONS

English Language Translation of CN 100523158 C.*

(Continued)

*Primary Examiner* — Bethany Barham
*Assistant Examiner* — Dominic Lazaro
(74) *Attorney, Agent, or Firm* — Ella Cheong Hong Kong; Sam T. Yip (57) ABSTRACT

The present invention relates to a method of preparing a solid form of soy isoflavone (e.g. genistein). In particular, the present invention relates to a method of preparing a solid form of soy isoflavone by precipitation with compressed antisolvent using a supercritical fluid to produce nano-sized particles of soy isoflavone with an improved dissolution rate and bioavailability. An oral composition or aerosolized formulation comprising the nanoparticles of the soy isoflavone prepared by the method of the present invention is also disclosed herein. The dissolution rate and bioavailability of the nanoparticles of the soy isoflavone prepared by the method of the present invention have a 2-fold increase and a 2.6-fold increase respectively as compared to those of the raw soy isoflavone.

11 Claims, 10 Drawing Sheets

(56) References Cited

U.S. PATENT DOCUMENTS 7,332,111 B2 2/2008 Grothe et al.
2004/0071781 A1* 4/2004 Chattopadhyay et al. .... 424/489

OTHER PUBLICATIONS

Walter, E.D., Genistin (an Isoflavone Glucoside) and its Aglucone, Genistein, from Soybeans, J. Am. Chem. Soc., 63 (1941) pp. 3273-3276.*

Andre'anne Bouchard et al., "Effect of the spraying conditions and nozzle design on the shape and size distribution of particles obtained with supercritical fluid drying" European Journal of Pharmaceutics and Biopharmaceutics, 2008, 70(1), 389-401.

Mariana Sousa Costa et al., "Supercritical antisolvent precipitation of PHBV microparticles", International Journal of Pharmaceutics, 2007, 328(1), 72-77.

Sandra Apers et al., "Fast high-performance liquid chromatography method for quality control of soy extracts", Journal of Chromatography A, 2004, 1038(1-2), 107-117.

Daruházi A.E. et al., "Utility of Cyclodextrins in the Formulation of Genistein Part 1. Preparation and Physicochemical Properties of Genistein Complexes with Native Cyclodextrins", Journal of Pharmaceutical and Biomedical Analysis, 2008, 48(3), 636-640.

Seung-Hyun Lee et al., "Enhanced Bioavailability of Soy Isoflavones by Complexation with Beta-Cyclodextrin in Rats", Biosci. Biotechnol. Biochem., 2007, 71(12), 2927-2933.

Nusrat Motlekar et al., "Preparation and Characterization of Genistein Containing Poly(ethylene glycol) Microparticles", Journal Applied Polymer Science, 2006, 101(3), 2070-2078.

Candy Lin et al., "Producing Nanoparticles Using Precipitation with Compressed Antisolvent", Ind. Eng. Chem. Res., 2007, 46(11), 3580-3589.

E. Reverchon et al., "Tailoring of Nano- and Micro-Particles of Some Superconductor Precursors by Supercritical Antisolvent Precipitation", Journal of Supercritical Fluids, 2002, 23(1), 81-87.

M. A. Rostango et al., "Pressurized liquid extraction of isoflavones from soybeans", Analytica Chimica Acta, 2004, 522(2), 169-177.

Stancanelli et al, "The Enhancement of Isoflavones Water Solubility by Complexation with Modified Cyclodextrins: A Spectroscopic Investigation with Implications in the Pharmaceutical Analysis", Journal of Pharmaceutical and Biomedical Analysis, 2007, 44(4), 980-984.

Chang, Alan A. L. (2006), "Study of Particle Formation Using Supercritical $CO_2$ As an Antisolvent", A dissertation submitted to the Graduate Faculty of North Carolina State University for the Degree of Doctor of Philosophy, Chemical Engineering Programme.

2nd Office Action of CN201310027175.7 issued from the State Intellectual Property Office of the People's Republic of China on Jan. 12, 2015.

Li et al., "Supercritical Fluid Precipitation Technology and Its Use in Preparation of Pharmaceuticals", Chinese Journal of Hospital Pharmacy, 2009, 29(18).

* cited by examiner

METHOD OF PREPARING SOY ISOFLAVONE NANOPARTICLES BY PRECIPITATION WITH COMPRESSED ANTISOLVENT (PCA) USING A SUPERCRITICAL FLUID

CROSS-REFERENCE TO RELATED APPLICATIONS

The present application claims priority from the U.S. provisional application Ser. No. 61/632,212 filed Jan. 20, 2012, the disclosure of which is incorporated herein by reference.

FIELD OF THE INVENTION

The present invention relates to a method of preparing a solid form of soy isoflavone (a subclass of flavonoid characterized in soybeans or soybean products). In particular, the present invention relates to a method of preparing a solid form of soy isoflavone (e.g. genistein and its derivatives) by precipitation with compressed antisolvent (PCA) using a supercritical fluid to produce nano-sized particles of soy isoflavone with an improved dissolution rate and bioavailability. The present invention also relates to a composition comprising the soy isoflavone nanoparticles for oral administration or for aerosol inhalation.

TECHNICAL BACKGROUND

Oral route is the most common route of drug administration. The drug delivered by oral administration is usually in the form of powder, tablet or capsule, and is first dissolved in the gastrointestinal fluid along the GI tract and the dissolved drug subsequently permeates through the gastrointestinal membrane. However, oral route is not suitable for many drug molecules because of unacceptably low bioavailability caused by low water solubility, poor gastrointestinal membrane permeability, first pass metabolism, and instability in the gastrointestinal environment.

Soy isoflavones are phytoestrogens with chemical structures and physiological functions that are similar to those of the female hormone, estrogen. Thus, they can relieve estrogen-deficient diseases especially menopausal symptoms including hot flashes, osteoporosis and cardiovascular problems. To date, twelve main isoflavones have been characterized in soy bean or soy bean products including genistein, daidzein, and glycitein (aglycones), and their respective malonyl, acetyl, and glucosyl forms (glucosides) (Apers et al. 2004; Rostagno et al. 2004). Although isoflavones (e.g. Genistein) have been widely used as healthcare products to relieve estrogen-deficient diseases especially menopausal symptoms, their therapeutic effects may be hampered by its poor water solubility. In order to improve its water solubility, some research groups have tried to form complexes between genistein and different carriers such as cyclodextrins (Lee et al. 2007; Stancanelli et al. 2007; Daruhazi et al. 2008) and PEG (Motlekar et al. 2006). However, these methods have limitations such as high residual organic solvent content, the instability of drugs and carriers as well as the safety issues of the carrier materials. Thus, there still remains a need for a process which can produce a dosage form of soy isoflavone with improved water solubility and bioavailability.

A way to increase the dissolution rate of poorly water soluble drugs is through the increase in the total surface area by reducing the drug particle size. Different techniques have been applied for this purpose, including spray drying, freeze-drying, milling, liquid anti-solvent crystallization and precipitation with supercritical fluid. Compared to other techniques, supercritical fluid-based technology has attracted a great deal of attention because of the following four major advantages: (1) controlled particle size and distribution, (2) low cost and environmentally benign properties, (3) no degradation of product due to mechanical or thermal stresses relatively because of the mild operating conditions (Tc=31.1° C., Pc=7.38 MPa), (4) no contamination due to the presence of organic solvents. Among the supercritical fluid based processes for producing fine particles, precipitation with compressed antisolvent (PCA) using supercritical $CO_2$ has attracted a vast amount of attention. U.S. Pat. No. 5,874,029 (Subramaniam; Bala et al. 1999), U.S. Pat. No. 6,319,521 (Randolph; Theodore W. et al. 2001), U.S. Pat. No. 7,332,111 (Grothe; Willy et al. 2008), disclosed PCA process for producing fine particles. However, none of these conventional methods have achieved a significant particle size reduction with proof of improvements in the dissolution rate and bioavailability of the active ingredients being atomized into fine particles. Therefore, there is a need for providing an optimized PCA process to produce a desirable nanoparticle of soy isoflavone with significant particle size reduction and improved dissolution rate/bioavailability suitable for both oral and inhalable administrations.

SUMMARY OF THE INVENTION

The first aspect of the present invention is to provide a method for the production of soy isoflavone nanoparticles with an improved dissolution rate and bioavailability. In the presently disclosed method, precipitation with compressed antisolvent (PCA) using supercritical $CO_2$ is employed to precipitate soy isoflavone for particle size reduction to improve its dissolution rate and oral bioavailability. The method of the present invention can improve water solubility of any intended substance under the soy isoflavone subclass in order for generating more efficacious pharmaceuticals and health care products. The second aspect of the present invention is to provide a composition comprising the soy isoflavone nanoparticles with improved dissolution rate and bioavailability which are prepared by the presently disclosed method.

In the present invention, the dissolution rate and oral bioavailability of the soy isoflavone (e.g. genistein) are increased by the particle size reduction using the PCA process. Process variables such as precipitation pressure, drug solution concentration and feed rate ratio of supercritical $CO_2$ to solution of intended substance, which could affect particle size and particle size distribution of soy isoflavone are investigated. The physicochemical properties of the particles before and after the PCA process in the solid state are characterized by powder X-ray diffraction (XRD) and differential scanning calorimetry (DSC). Dissolution rate experiments and oral bioavailability studies in rats are performed to compare the absorption of processed and unprocessed genistein particles.

In the first aspect of the present invention, the method includes: providing a supercritical fluid to a precipitation chamber where the precipitation of a soy isoflavone will take place; dissolving raw soy isoflavone into an organic solvent to form a solution of soy isoflavone; presetting conditions in the precipitation chamber such as pressure, temperature and feed rate ratio of the supercritical fluid: the soy isoflavone solution; introducing the soy isoflavone solution into the precipitation chamber through a co-axial nozzle after the preset conditions are reached; the formation of fine solid particles containing the soy isoflavone due to a sharp rise in supersaturation by mixing the supercritical fluid and the soy isoflavone solution in the precipitation chamber; removing the organic solvent residue from the resulted particles by pumping excess supercritical fluid into the chamber after stopping the solution pump; collecting the fine solid particles containing the soy isoflavone from a metal filter situated at the bottom of the precipitation chamber after gradual depressurization to atmospheric pressure in the precipitation chamber; further removing the organic solvent through a low pressure cyclone separator. The excess supercritical fluid turns into vapor which is removed from the precipitation chamber through a vent at the low pressure cyclone separator. In an exemplary embodiment, the soy isoflavone used in the present invention is soy aglycone isoflavone including genistein, daidzein, and glycitein. Other soy isoflavone such as soy glucoside isoflavone including daidzin, glycitin, genistin, acetyldaidzine, acetylglycitin, acetylgenistin, malonyldaidzin, malonylglycitin, and malonylgenistin may also be used in the present invention to be precipitated into particle according to the method of the present invention.

In the second aspect of the present invention, a composition comprising soy isoflavone nanoparticles prepared by the method of the present invention is also provided. The soy isoflavone nanoparticles has at least 2-fold increase in the dissolution rate and about 2.6-fold increase in bioavailability as compared to raw soy isoflavone. By using the optimal operating conditions such as the optimal pressure, temperature and feed rate ratio of the supercritical fluid to the solution containing soy isoflavone, the width of the particles can be reduced by up to about 50-200 times. The average width of the genistein particle is less than 1 μm. More preferably, the average width of the genistein particle is less than 260 nm.

DEFINITIONS

As used herein, the term "compressed antisolvent" refers to the supercritical or near supercritical $CO_2$.

As used herein, the term "soy isoflavone" refers to the soy aglycone isoflavone, e.g., genistein, daidzein, and glycitein, etc., or their respective malonyl, acetyl, and glucosyl forms/ soy glucoside isoflavone, e.g., daidzin, glycitin, genistin, acetyldaidzine, acetylglycitin, acetylgenistin, malonyldaidzin, malonylglycitin, and malonylgenistin, etc.

As used herein, the term "nanoparticles" means the particles having an average width of less than 1 μm. More preferably, the average width of the particles is less than 200 nm.

As used herein, the term "width" refers to the shortest length of the particles as inferred from scanning electron microscopy (SEM) images.

As used herein, the concentration of genistein means the concentration of the genistein dissolved in an organic solvent such as acetone at room temperature and atmospheric pressure. The saturation point of genistein concentration dissolved in acetone at room temperature and atmospheric pressure is 4 mg/mL.

As used herein, "pressure" or "precipitation pressure" refers to a pressure from subcritical phase to supercritical phase, that is below or above 73.8 bar, respectively, or as defined in any specific embodiments. In the experimental setup of the present invention, the lower limit of the subcritical phase pressure that can be achieved is about 60 bar while the upper limit of the supercritical phase pressure is about 350 bar.

DETAILED DESCRIPTION OF THE INVENTION

The present invention describes a method of using precipitation with compressed antisolvent (PCA) process to produce soy isoflavone nanoparticles with improved dissolution rate and bioavailability. The impact of various process parameters—pressure of precipitation, concentration of initial drug solution and feed rate ratio of $CO_2$/drug solution—on particle formation is evaluated. Among these parameters, pressure is the most important parameter that greatly affects the particle size and morphology. Under the optimized operating conditions, the width of the soy isoflavone nanoparticles is reduced from about 10-50 μm to about 200-250 nm (which is about 50 to 200 times reduction in size). The physicochemical properties of the resulting nanoparticles has been analyzed by characterization techniques, including scanning electron microscopy (SEM), differential scanning calorimetry (DSC), X-ray diffraction (XRD) and dissolution rate study. The 24-hour pharmacokinetic study performed in rats shows that the bioavailability of nano-sized genistein is about 2.6 fold higher than that of the unprocessed soy isoflavone (raw soy isoflavone).

EXAMPLES

The present invention is explained more specifically by referring to the following examples. These examples are given only for a better understanding of the present invention, and not intended to limit the scope of the invention in any way.

Example 1

Figure 1:
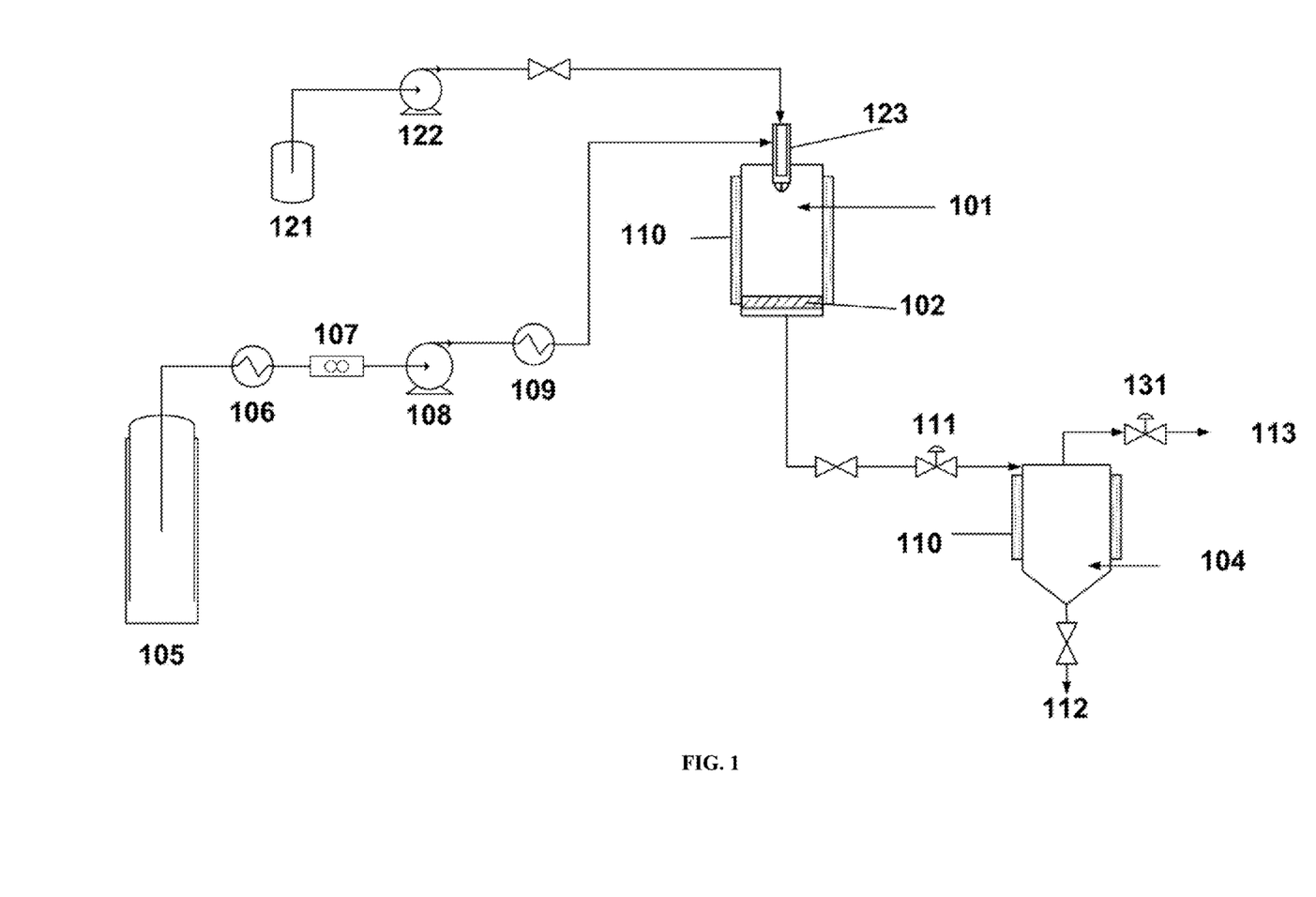
FIG. 1 is a schematic diagram of the system for the PCA process.

The system setup for the PCA process is shown in FIG. 1 (Lin et al. 2007). The $CO_2$ tank 105 is connected to a cooler 106 in order to maintain the $CO_2$ in the liquid phase prior to raising it to the desired temperature in a heater. The cooler 106 can be a water/ethylene glycol circulating bath at −4° C. A flow meter 107 is used to monitor the $CO_2$ flow rate. A high-performance pump 108 is used to deliver the fluid through a heater 109 into a precipitation chamber 101 which is surrounded by a heating jacket 110 and incorporated with a top-mounted co-axial nozzle 123. On the other end of the co-axial nozzle 123, it is connected to a solution tank 121 and a solution pump 122 for the dissolving an optimal concentration of soy isoflavone, e.g. genistein, into an organic solvent and pumping the solution of soy isoflavone into the precipitation chamber 101. In an exemplary embodiment, the volume of the precipitation chamber 101 is about 100 mL. A metal filter 102 having a pore size of 5 μm is situated at the bottom of the precipitation chamber 101 for collecting the particles when they are formed after the PCA process. A back-pressure regulator 111 is connected to the outlet of the precipitation chamber 101 and a lower pressure cyclone separator 104 where the remaining organic solvent are collected from the precipitation chamber 101 while the excess $CO_2$ from the precipitation chamber 101 is vented out through a vent 131 which is connected to the low pressure cyclone separator 104. Precipitation pressure, temperature and $CO_2$ flow rate are all controlled by a computerized system governing the whole PCA system.

In an exemplary embodiment, supercritical $CO_2$ is first prepared from the $CO_2$ module including the $CO_2$ tank, cooler, flow meter, high performance pump and heater. A flow of supercritical $CO_2$ is then pumped from the $CO_2$ module into the precipitation chamber as a compressed antisolvent for the precipitation of the intended substance to take place. The intended substance to be precipitated, i.e. genistein, is first dissolved in an organic solvent, e.g. acetone, in an optimal concentration ranging from 0.4-4 mg/mL. Once the preset conditions such as the precipitation pressure, temperature and feed rate ratio of the supercritical $CO_2$ to the genistein solution ranging from 30-90 g/mL are reached, the genistein solution dissolving in acetone are introduced into the precipitation chamber through a co-axial nozzle. When the genistein solution in acetone are mixed with the supercritical $CO_2$ in the precipitation chamber under an optimal temperature from 31° C. to 60° C., preferably 40° C., and at a precipitation pressure from subcritical pressure to supercritical pressure, i.e., 60 to 350 bar, more preferably 70 to 120 bar, a sharp rise in the supersaturation occurs within the liquid mixture and leads to the formation of fine solid particles which contain genistein. The particles are thoroughly washed and the solvent residue is removed by pumping supercritical $CO_2$ for another 30 minutes after stopping the solution pump. The particles are then collected from the metal filter situated at the bottom of the precipitation chamber after the gradual depressurization of the precipitation chamber to atmospheric pressure. Finally, the organic solvent is recollected from the bottom of the low pressure cyclone separator while the vapor is vented out of the system.

Example 2

To investigate the effect of pressure, concentration of genistein and feed rate ratio of the supercritical fluid on particle formation, a pressure varying between 70 to 120 bar is applied; 0.4 mg/mL to 4 mg/mL of genistein is dissolved in the acetone; molar fraction of $CO_2$ in the combined feed to the precipitation chamber is maintained at 99.0 mol %.

Figure 2:
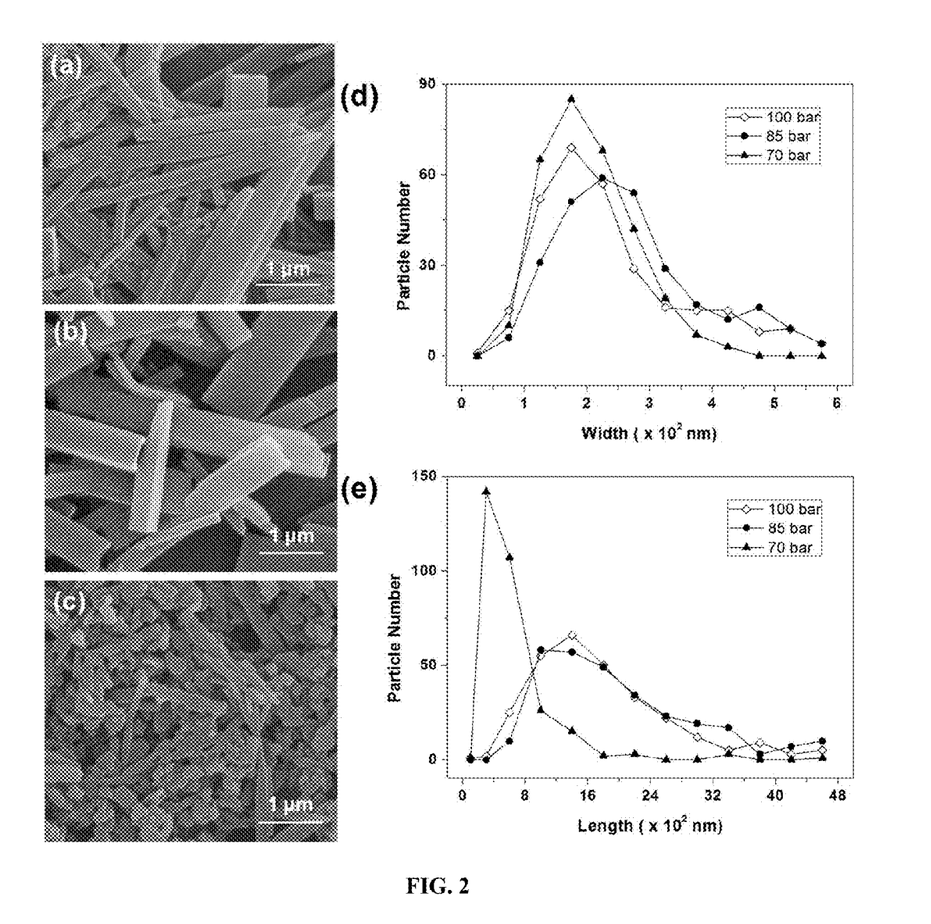
FIG. 2 shows the effect of different precipitation pressures on genistein particle formation at the initial genistein concentration of 4 mg/mL with respects to the particle morphology and particle size distribution: SEM images of genistein particles obtained from (a) 100 bar (Run 4), (b) 85 bar (Run 5) and (c) 70 bar (Run 6) and particle size distribution in terms of (d) width and (e) length.
Figure 3:
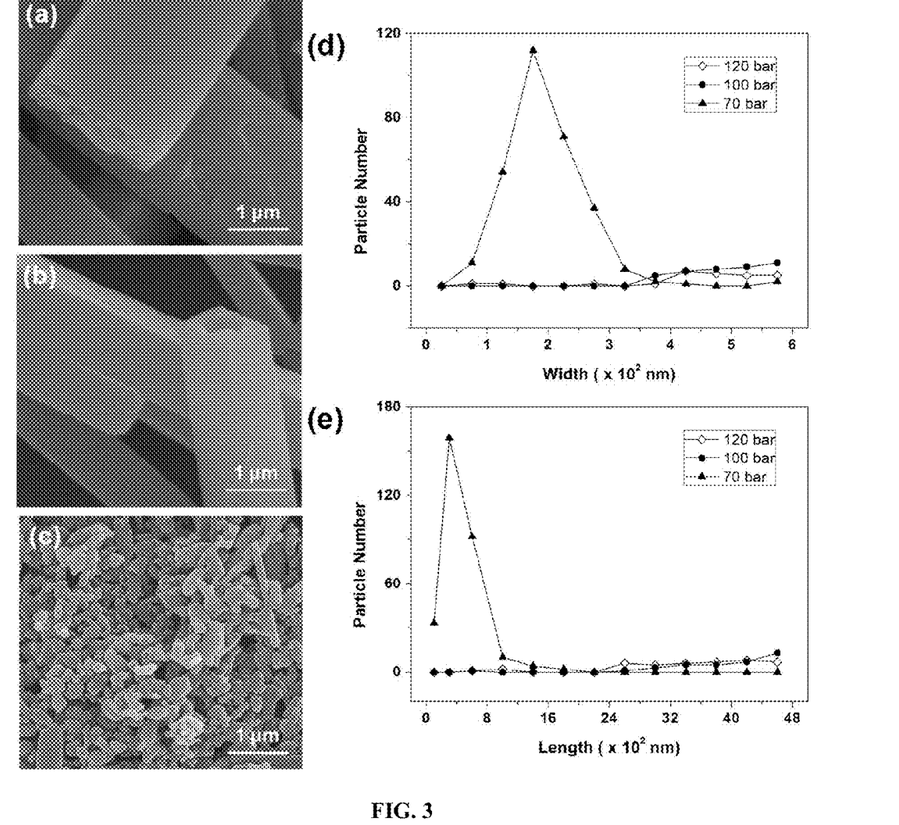
FIG. 3 shows the effect of different precipitation pressures on genistein particle formation at the initial genistein concentration of 0.4 mg/mL with respects to the particle morphology and particle size distribution: SEM images of genistein particles obtained from (a) 120 bar (Run 1), (b) 100 bar (Run 2) and (c) 70 bar (Run 8) and particle size distribution in terms of (d) width and (e) length.

FIG. 2 shows the results when the genistein concentration is set at 4 mg/mL. Almost all the particles generated at higher pressures of 100 and 85 bar are in rectangular rod shape (FIGS. 2a & 2b, respectively), while rod-like particles are obtained at 70 bar (FIG. 2c). The width and length of the particle are measured from at least 300 particles from each run and their average values are summarized in Table 1. The length to width ratio (L/W) of the rectangular rods is between 8.3-8.5 at 85 bar and 100 bar, but the ratio is 3.1 at 70 bar (Table 1). The width and length distribution of the particles are displayed in FIGS. 2d and 2e, respectively. The most distinguishing feature is the large number of partially agglomerated small rod-shaped particles at 70 bar which may be the main contributor to the reduced L/W ratio at this low pressure. Similar phenomenon is observed when the genistein concentration is set at 0.4 mg/mL except that at 0.4 mg/mL the particles are much larger at higher pressure such as 100 and 120 bar (FIGS. 3a, 3b, and 3c). The width and length distribution are shown in FIGS. 3d and 3e, respectively. Again, there are a large number of partially agglomerated rod-like particles prepared under 70 bar.

TABLE 1

| Run | Pressure (bar) | Genistein Concentration (mg/mL) | Feed Rate Ratio (R) (g/mL) ($CO_2$/genistein solution) | Width, W ≤200 nm (% of total particle number) | Length, L ≤1000 nm (% of total particle number) | L/W Ratio ± SD |
|---|---|---|---|---|---|---|
| 1 | 120 | 0.4 | 30/0.5 (R = 60) | 0.7% | 1.0% | 9.2 ± 4.7 |
| 2 | 100 | 0.4 | 30/0.5 (R = 60) | 0.0% | 0.3% | 10.8 ± 5.4 |
| 3 | 100 | 2 | 30/0.5 (R = 60) | 3.7% | 1.3% | 9.8 ± 6.0 |
| 4 | 100 | 4 | 30/0.5 (R = 60) | 45.7% | 16.3% | 8.5 ± 4.4 |
| 5 | 85 | 4 | 30/0.5 | 29.3% | 9.3% | 8.3 ± 4.6 |

TABLE 1-continued

| Run | Pressure (bar) | Genistein Concentration (mg/mL) | Feed Rate Ratio (R) (g/mL) (CO$_2$/genistein solution) | Width, W ≤200 nm (% of total particle number) | Length, L ≤1000 nm (% of total particle number) | L/W Ratio ± SD |
|---|---|---|---|---|---|---|
| 6 | 70 | 4 | 30/0.5 (R = 60) | 53.3% | 89.0% | 3.1 ± 2.6 |
| 7 | 70 | 2 | 30/0.5 (R = 60) | 43.0% | 90.7% | 2.7 ± 2.7 |
| 8 | 70 | 0.4 | 30/0.5 (R = 60) | 59.7% | 97.7% | 2.1 ± 1.5 |
| 9 | 70 | 0.4 | 30/1 (R = 30) | 6.7% | 40.7% | 4.8 ± 4.1 |
| 10 | 70 | 0.4 | 30/0.33 (R = 90) | 69.0% | 100% | 1.7 ± 0.7 |

Example 3

Figure 4:
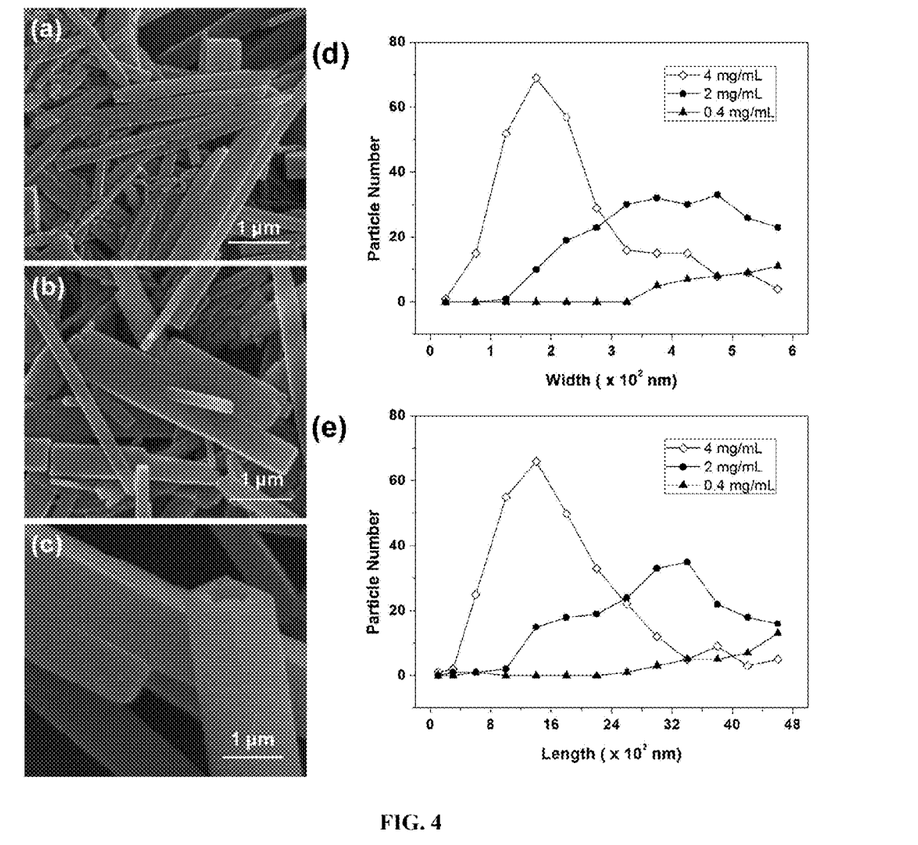
FIG. 4 shows the effect of different initial genistein concentrations on genistein particle formation at a precipitation pressure of 100 bar with respects to the particle morphology and particle size distribution: SEM images of genistein particles obtained from (a) 4 mg/mL (Run 4), (b) 2 mg/mL (Run 3) and (c) 0.4 mg/mL (Run 2) and particle size distribution in terms of (d) width and (e) length.
Figure 5:
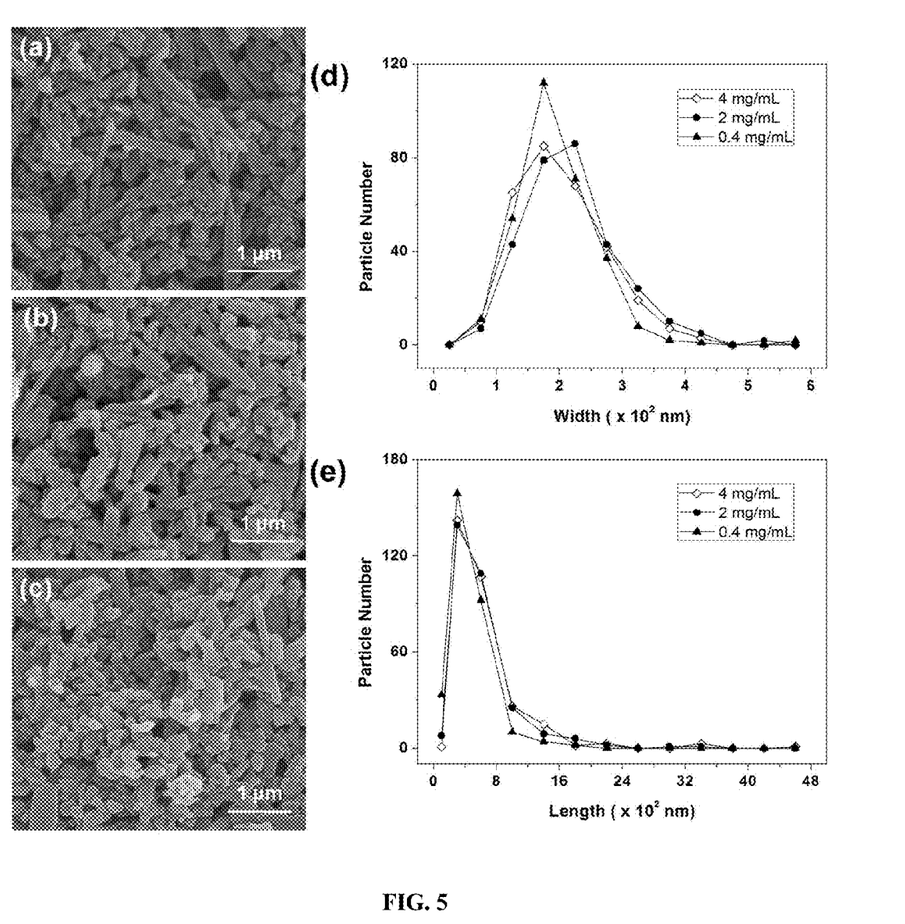
FIG. 5 shows the effect of different initial genistein concentrations on genistein particle formation at a precipitation pressure of 70 bar with respects to the particle morphology and particle size distribution: SEM images of genistein particles obtained from (a) 4 mg/mL (Run 6), (b) 2 mg/mL (Run 7) and (c) 0.4 mg/mL (Run 8) and particle size distribution in terms of (d) width and (e) length.

The effect of increasing genistein concentration from 0.4 mg/mL to 4 mg/mL on particle size formation at two pressures of 100 bar and 70 bar under a feed rate ratio (R) of 60 is evaluated. It is found that the particle size is more sensitive to the genistein concentration when the pressure is set at 100 bar than that at 70 bar. At higher pressure such as 100 bar, increasing the genistein concentration from 0.4 mg/mL to 4 mg/mL result in a reduction in particle size and a reduction in the L/W ratio from 10.8 to 8.5 (FIG. 4 and Run nos. 2-4 in Table 1). In contrast, at lower pressure such as 70 bar, reducing genistein concentration from 4 mg/mL to 0.4 mg/mL could slightly decrease the particle size with a reducing L/W ratio from 3.1 to 2.1 (FIG. 5 and Run nos. 6-8 in Table 1). The change of genistein particle size as well as its morphological change are determined by two competing effects: nucleation and particle growth (Reverchon et al. 2002). At 100 bar, when a more concentrated solution is introduced into the system, there is a higher supersaturation. This leads to a faster nucleation rate, more nuclei and smaller particles. A reversing effect of the increasing genistein concentration on particle formation at 70 bar may be due to a different principle which dominates the process of nucleation and particle growth in the system when the operating point is below the mixture critical point. From these data, pressure at 100 bar is shown to be more optimal than pressure at 70 bar in terms of the nucleation rate and more favorable to supersaturation when the genistein concentration is high, which is important to the particle formation.

Example 4

The influence of the feed rate ratio (R) on genistein particle size at a fixed pressure of 70 bar and a fixed genistein solution concentration of 0.4 mg/mL is evaluated. The feed rate ratio ranges from 30 to 90 g/mL, which corresponds to a mole fraction of 2.0% to 0.7% of acetone in the system.

Figure 6:
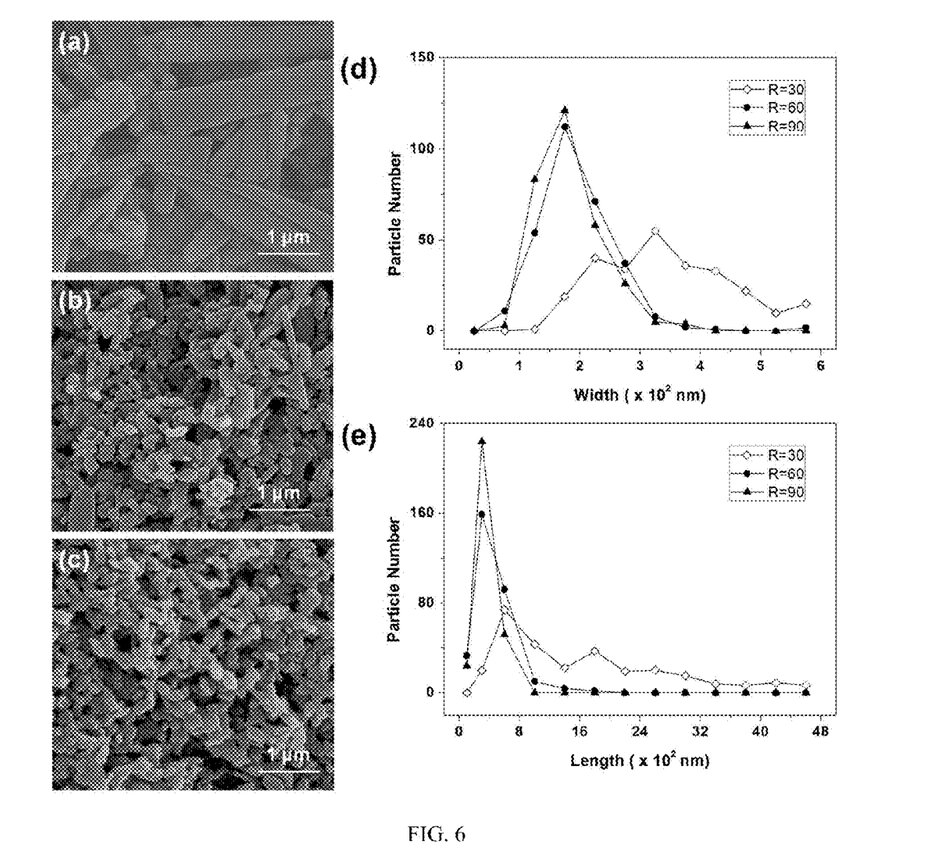
FIG. 6 shows the effect of different feed rate ratios on genistein particle formation at a precipitation pressure of 70 bar with respects to the particle morphology and particle size distribution: SEM images of genistein particles obtained from (a) R=30 (Run 9), (b) R=60 (Run 8) and (c) R=90 (Run 10) and particle size distribution in terms of (d) width and (e) length.

When feed rate ratio (R) is at 30 g/mL, elongated rectangular particles are formed (FIG. 6a); short rod-shaped particles are obtained when R is at 60 or 90 g/mL (FIGS. 6b & 6c). The particle width and length distributions displayed in FIGS. 6d and 6e clearly show the significantly smaller particles at the higher value of R.

Example 5

Figure 7:
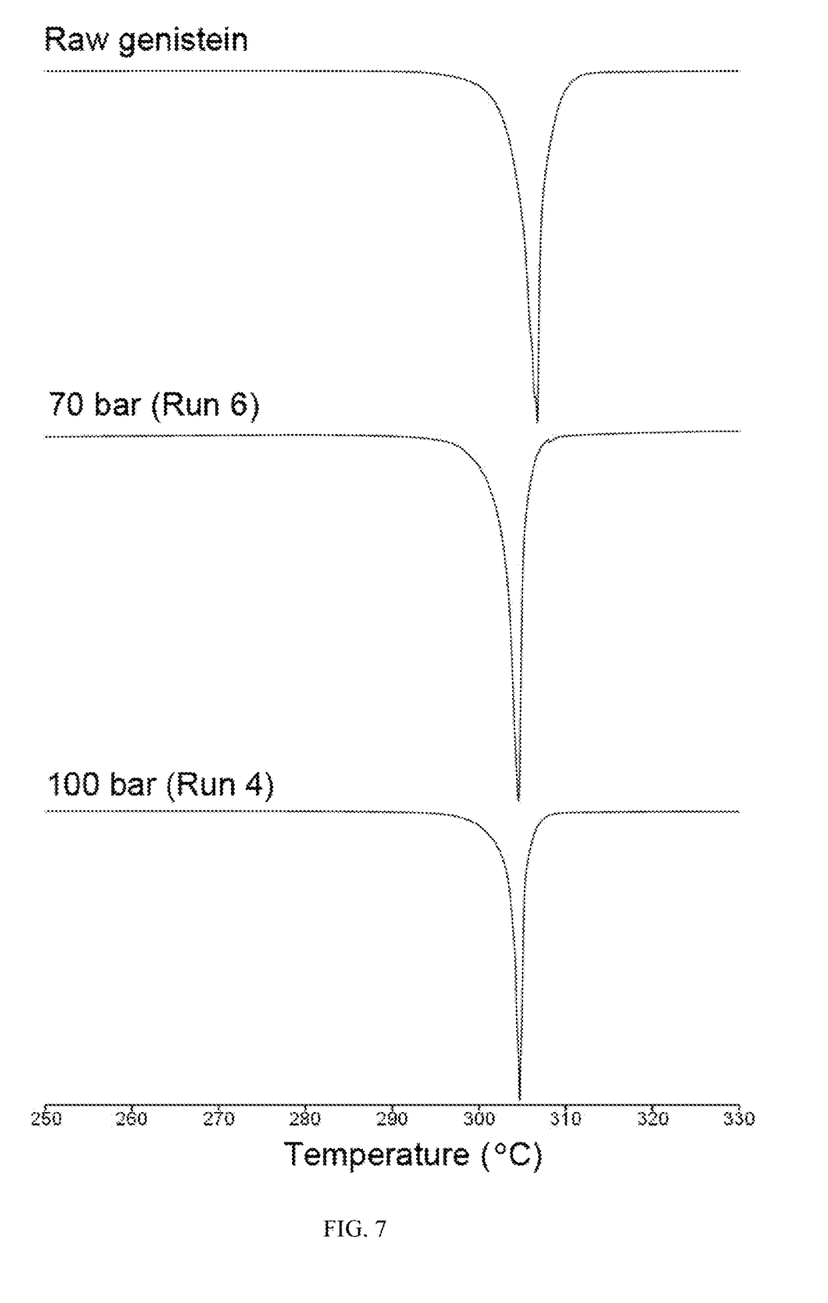
FIG. 7 is DSC thermograms of raw genistein versus PCA processed genistein.
Figure 8:
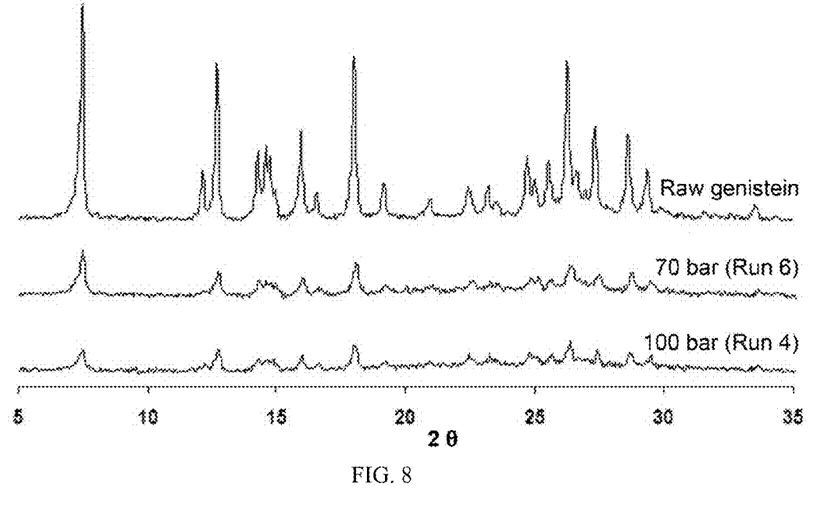
FIG. 8 is powder X-ray diffraction patterns of raw genistein versus PCA processed genistein.

Processed genistein from Run 6 (70 bar) and Run 4 (100 bar) together with unprocessed genistein are analyzed by DSC (FIG. 7). The melting temperature of all samples is 304° C., indicating that the PCA process does not influence the chemical structure of genistein particles. This conclusion is corroborated with the results from XRD (FIG. 8). The characteristic diffraction peaks are observed to be located at the same positions in the span of 2θ, indicating that the crystal structure of genistein remains after PCA process. However, the intensity of all the peaks in the processed genistein samples reduce considerably compared to that of raw genistein.

Example 6

Figure 9:
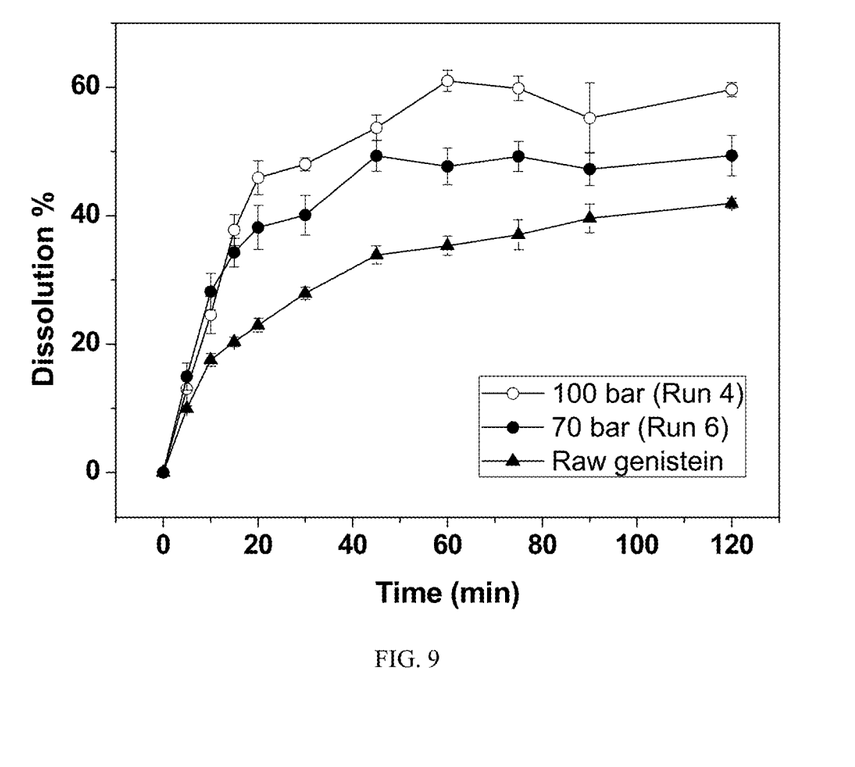
FIG. 9 is dissolution profiles of raw genistein versus PCA processed genistein under different pressures of 70 bar (Run 6) and 100 bar (Run 4).

The dissolution rate of genistein from the PCA process is significantly increased in comparison with the unprocessed genistein (FIG. 9). 46% weight percentage of the processed genistein from Run 4 (100 bar) is dissolved in a dissolution medium while only 23% of the unprocessed genistein is dissolved over a period of 20 minutes. This 2-fold increase in dissolution rate can be credited to the reduction in particle size resulting in an increase in total surface area. However, the dissolution rate for particles which are obtained at 70 bar with smaller particles (Run 6) is slower than that of particles obtained at 100 bar (Run 4).

Example 7

Figure 10:
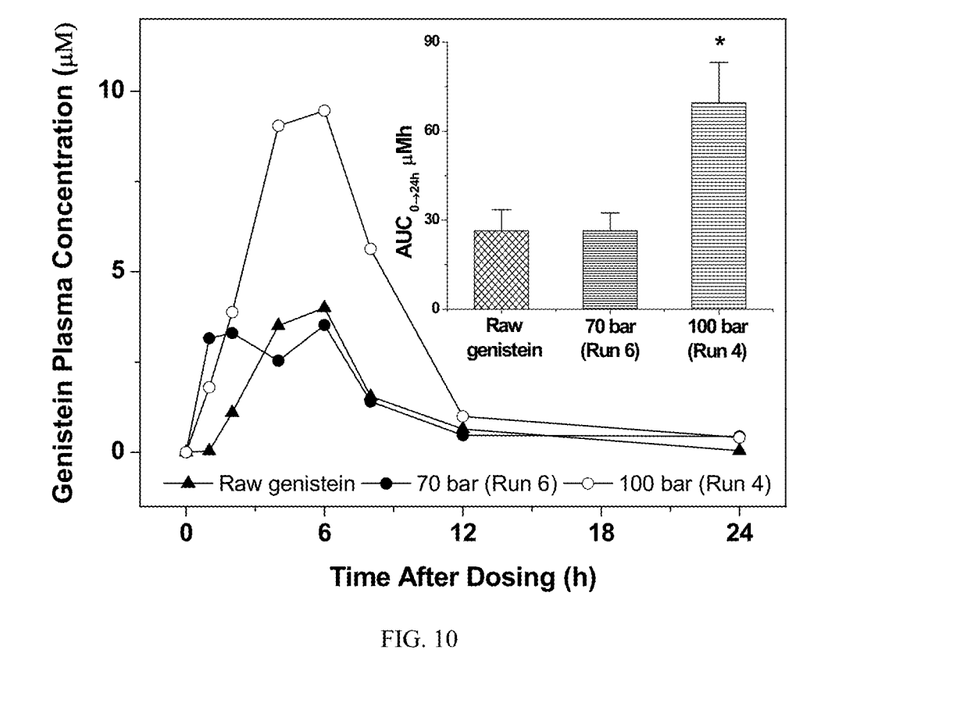
FIG. 10 is the plasma concentration-time profiles of raw genistein versus PCA processed genistein under different pressures at 70 bar and 100 bar which are obtained from one representative rat of each of three groups and $AUC_{0 \to 24h}$ (right upper panel) is obtained from all 4 rats of each group *, $P<0.05$.

The in vivo bioavailability results are shown in FIG. 10. The plasma concentration-time profile shows that $C_{max}$ (i.e. maximum plasma concentration) of genistein particles obtained at 100 bar is 2.4 times larger than that of raw genistein, while those obtained at 70 bar is about the same as that of raw genistein. T. (i.e., the time of $C_{max}$) of processed genistein at 100 bar is the same as that of raw genistein while two subsequent plasma peaks shown in the particles that obtained at 70 bar. The inset bar chart shows that the $AUC_{0 \to 24h}$ (area under curve) of the rectangular rod shape genistein particles obtained at 100 bar is 2.6 times higher than that of unprocessed genistein and the partially agglomerated rod-shaped particles obtained at 70 bar.

If desired, the different functions discussed herein may be performed in a different order and/or concurrently with each other. Furthermore, if desired, one or more of the above-described functions may be optional or may be combined.

Although various aspects of the invention are set out in the independent claims, other aspects of the invention comprise other combinations of features from the described embodiments and/or the dependent claims with the features of the independent claims, and not solely the combinations explicitly set out in the claims.

It is also noted herein that while the above describes exemplary embodiments of the invention, these descriptions should not be viewed in a limiting sense. Rather, there are several variations and modifications which may be made without departing from the scope of the present invention as defined in the appended claims.

What we claim:

1. A method of preparing elongated soy isoflavone nanoparticles having a length/width ratio of 8.3 to 10.8 for improving in vivo bioavailability based on precipitation with compressed antisolvent, the method comprising:
providing a supercritical fluid as the compressed antisolvent to a precipitation chamber where said precipitation of the elongated soy isoflavone nanoparticles takes place, wherein said supercritical fluid is supercritical or near supercritical $CO_2$;
dissolving raw soy isoflavone in to an organic solvent to form a solution of soy isoflavone at a concentration of 0.4 mg/mL to 4 mg/mL, wherein said organic solvent is acetone;
presetting said precipitation chamber to reach conditions comprising a temperature ranging of 31° C. to 60° C., and a pressure ranging of 85 to 120 bar;
introducing said solution of soy isoflavone into the precipitation chamber through a co-axial nozzle after the conditions are reached in said precipitation chamber;
mixing said supercritical fluid and said solution of soy isoflavone in said precipitation chamber to precipitate said elongated soy isoflavone nanoparticles with size reduction from the dissolved raw soy isoflavone in the organic solvent under the conditions in said precipitation chamber, wherein a feed rate ratio of said supercritical fluid to said solution of soy isoflavone ranges from 30 to 90 g/mL;
providing excess supercritical fluid into the precipitation chamber to remove remaining organic residue from said elongated soy isoflavone nanoparticles; and
collecting said elongated soy isoflavone nanoparticles from a metal filter at the bottom of said precipitation chamber after gradual depressurization to atmospheric pressure in said precipitation chamber.

2. The method of claim 1, wherein said raw soy isoflavone is soy aglycone isoflavone selected from the group consisting of genistein, daidzein, glycitein, or soy glucoside isoflavone selected from the group consisting of daidzin, glycitin, genistin, acetyldaidzin, acetylglycitin acetylgenistin malonyldaidzine, malonylglycitin, and malonylgenistin.

3. The method of claim 1, wherein said solution of soy isoflavone has a concentration of said raw soy isoflavone in the acetone at room temperature and atmosphere pressure from ten times lower than a saturation point of said solution of soy isoflavone to said saturation point.

4. The method of claim 3, wherein said saturation point is 4 mg/mL in the acetone.

5. The method of claim 1, wherein said temperature is 40° C.

6. The method of claim 1, wherein said elongated soy isoflavone nanoparticles have about 50-200 times reduction in an average width, comparing with the raw soy isoflavone when the conditions preset in said precipitation chamber reach a temperature of 40° C., a feed rate ratio of the supercritical fluid to the soy isoflavone solution at 60 g/mL, and 4 mg/mL of the raw soy isoflavone in the solution of soy isoflavone is used.

7. The method of claim 6, wherein said elongated soy isoflavone nanoparticles have an average width of less than 1 μm.

8. The method of claim 6, wherein said elongated soy isoflavone nanoparticles have an average width of less than 260 nm.

9. The method of claim 1, wherein the pressure is about 100 bar for providing the elongated soy isoflavone nanoparticles having a 2-fold increase in dissolution rate, and a 2.6-fold increase in bioavailability as compared with that of the raw soy isoflavone.

10. The method of claim 1, further comprising:
recollecting the organic solvent from a low pressure cyclone separator while the excess supercritical fluid turns into vapor in said low pressure cyclone separator and being vented out through a vent which is connected to said low pressure cyclone separator.

11. The method of claim 1, wherein the raw soy isoflavone is genistein, the supercritical fluid is supercritical carbon dioxide, the pressure is 100 bar, the concentration of said genistein is 0.4 mg/mL, the feed rate ratio is 60 g/mL, and the temperature is 40° C.

* * * * *